United States Patent [19]

Schmierer et al.

[11] Patent Number: 4,775,406
[45] Date of Patent: Oct. 4, 1988

[54] SALTS OF 1-PHENYLIMIDAZOLE-5-CARBOXYLIC ACIDS, COMPOSITION CONTAINING THEM, AND THEIR USE AS GROWTH REGULATORS

[75] Inventors: Roland Schmierer, Todtenweis; Ernst-Friedrich Schulze, Hofheim am Taunus; Helmut Büstell, Frankfurt am Main; Erwin Hacker, Hochheim am Main, all of Fed. Rep. of Germany

[73] Assignee: Hoechst Aktiengesellschaft, Frankfurt am Main, Fed. Rep. of Germany

[21] Appl. No.: 800,608

[22] Filed: Nov. 21, 1985

[30] Foreign Application Priority Data

Nov. 23, 1984 [DE] Fed. Rep. of Germany ....... 3442690

[51] Int. Cl.$^4$ .................. A01N 43/50; C07D 233/90; C07D 417/02
[52] U.S. Cl. ........................... 71/86; 71/90;
71/92; 540/450; 540/467; 540/470; 540/474;
540/484; 540/544; 540/545; 540/553; 540/554;
540/575; 540/612; 544/2; 544/3; 544/5; 544/8;
544/55; 544/60; 544/63; 544/65; 544/66;
544/67; 544/96; 544/139; 544/180; 544/182;
544/238; 544/333; 544/370; 546/278; 548/122;
548/123; 548/124; 548/125; 548/127; 548/128;
548/131; 548/134; 548/136; 548/143; 548/146;
548/206; 548/215; 548/240; 548/255; 548/262;
548/343
[58] Field of Search ............... 71/86, 90, 92; 540/450,
540/467, 470, 474, 484, 544, 545, 553, 554, 575,
612; 544/2, 3, 5, 8, 55, 60, 63, 65, 66, 67, 96,
139, 180, 182, 238, 333, 370; 546/278; 548/122,
123, 124, 125, 127, 128, 131, 134, 136, 143, 146,
206, 215, 240, 255, 262, 343

[56] References Cited
U.S. PATENT DOCUMENTS 4,437,875  3/1984  Howe et al. ..................... 71/92
4,525,202  6/1985  Large et al. .................... 71/86
4,554,013  11/1985  Los .............................. 71/92

FOREIGN PATENT DOCUMENTS 3217094  11/1983  Fed. Rep. of Germany ...... 548/343

Primary Examiner—Mary C. Lee
Assistant Examiner—Kurt G. Briscoe
Attorney, Agent, or Firm—Curtis, Morris & Safford

[57] ABSTRACT

The salts of 1-phenylimidazole-5-carboxylic acids substituted in the phenyl ring, of the general formula (I)

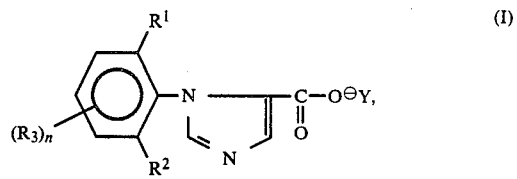

exhibit a good plant growth-regulating activity. In the general formula the symbols have the following meaning:

Y is an ammonium ion substituted up to fourfold by (substituted) alkyl, (substituted) alkenyl, alkynyl, (substituted) cycloalkyl, cycloalkenyl, and (substituted) phenyl, wherein the charged N may be part of a heterocyclic radial ($NH_4^+$ is excepted); phosphonium ion substituted fourfold by alkyl, (substituted) phenyl or (substituted) benzyl; sulfonium- or sulfoxonium ion substituted threefold by alkyl, (substituted) phenyl or (substituted) benzyl; the guanidinium ion or an O-alkylisourea cation;

$R^1$, $R^2$ independently of each other are alkyl;
$R^3$ is alkyl, alkoxy or halogen; and
n is 0, 1, 2 or 3.

In a process for the preparation of these salts, either the free carboxylic acid or one of the known metal salts (for example the sodium salt) is reacted with a compound Y' (Y'=Y minus H+), with a salt having Y as cation or with a hydroxide having Y as cation.

9 Claims, No Drawings

SALTS OF 1-PHENYLIMIDAZOLE-5-CARBOXYLIC ACIDS, COMPOSITION CONTAINING THEM, AND THEIR USE AS GROWTH REGULATORS

The invention relates to salts of 1-phenylimidazole-5-carboxylic acids with a cation derived in particular from an organic compound, a process for the preparation of said salts and their use as growth regulators.

1-Phenylimidazole-5-carboxylic acid derivatives substituted in the phenyl ring, and their use as growth regulators, are known from DE-A No. 3,217,094. In addition to the free acid and its esters, the compounds described also comprise those having the following general formula

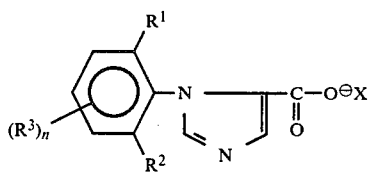

wherein the symbols have the following meaning:
X is a metal cation or ammonium;
$R^1$, $R^2$ independently of each other, are $C_1$–$C_4$-alkyl;
$R^3$ is $C_1$–$C_4$-alkyl, $C_1$–$C_4$-alkoxy or halogen, wherein the substituents can also be different, when n >1; and
n 0, 1, 2 or 3.

Examples of possible cations represented by X are metal cations such as those of Zn, Cu or Mn, alkali metal cations such as $Na^+$ and $NH_4^+$; among the compounds claimed, for example, is the sodium salt of 1-(2,6-dimethylphenyl)imidazole-5-carboxylic acid.

It is true that some of the known salts of 1-phenylimidazole-5-carboxylic acids exhibit adequate activity as growth regulators, but when these are used comparatively large amounts have to be employed, so that occasionally undesirable side effects can also occur.

It is therefore the object of the present invention to synthesize new, more active salts of 1-phenylimidazole-5-carboxylic acids, which can be used as growth regulators also in smaller amounts.

The invention proceeds from the known salts of 1-phenylimidazole-5-carboxylic acids substituted in the phenyl ring. The compounds according to the invention thus comprise those of the general formula (I)

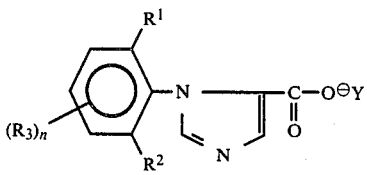 (I)

in which the symbols have the following meaning:
Y is

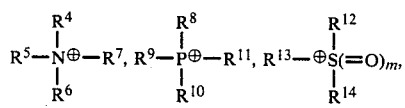

the argininium ion

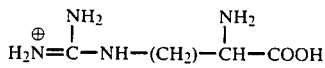

or the the guanidinium ion

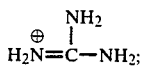

n is 0, 1, 2 or 3;
m is 0 or 1;
$R^1$, $R^2$ independently of each other are $C_1$–$C_4$-alkyl;
$R^3$ is $C_1$–$C_4$-alkyl, $C_1$–$C_4$-alkoxy or halogen, wherein, when n>1, the substituents can also be different;
$R^4$, $R^5$, $R^6$ independently of each other are H; $C_1$–$C_{18}$-alkyl which is unsubstituted or mono-, di- or trisubstituted, preferably monosubstituted, by halogen, $C_1$–$C_{12}$ alkoxy, preferably $C_1$–$C_6$-alkoxy, [$C_1$–$C_6$ alkoxy]-$C_2$–$C_4$ alkoxy, cyclo-$C_3$–$C_7$ alkyl, bicyclo-$C_7$–$C_{10}$-alkyl, benzyloxy, halobenzyloxy, methylbenzyloxy, benzyloxy-$C_2$–$C_4$-alkoxy, phenyl, halophenyl, methylphenyl, cyano, hydroxyl, formyl, $C_1$–$C_4$-alkylcarbonyl, carboxyl, $C_1$–$C_6$-alkoxycarbonyl, carbamoyl, phosphinyl, phosphonyl, $C_1$–$C_4$-alkylaminophosphonyl, di-$C_1$–$C_4$-alkylaminophosphonyl, amino, $C_1$–$C_6$-alkylamino, di-($C_1$–$C_6$-alkylamino), amino-$C_1$–$C_4$-alkylamino, $C_1$–$C_6$-alkylthio, phenylthio, phenoxy, furyl, tetrahydrofuryl imidazolyl or triazolyl; $C_3$–$C_6$-alkenyl unsubstituted or substituted by halogen or phenyl; $C_3$–$C_6$ alkynyl; cyclo-$C_3$–$C_8$-alkyl, unsubstituted or substituted by $C_1$–$C_4$-alkyl or halogen; cyclo-$C_5$–$C_6$ alkenyl; phenyl, unsubstituted, or mono-, di- or trisubstituted by halogen, nitro, cyano, $C_1$–$C_4$-alkyl, $C_1$–$C_4$-alkoxycarbonyl or $C_1$–$C_4$-alkoxy; or $R^4$ and $R^5$, together with the N atom, form a 5- to 8-membered saturated heterocyclic amino group in which, in addition to the one N, up to 2 C can be replaced by N, S and/or O, and which can be unsubstituted or substituted by $C_1$–$C_4$-alkyl, halogen, phenyl, benzyl, oxo, amino, $C_1$–$C_4$ alkylamino, di-$C_1$–$C_4$-alkylamino, amino-$C_1$–$C_4$-alkyl, hydroxyl, hydroxy-$C_1$–$C_4$-alkyl, and $C_1$–$C_4$-alkoxy;
$R^7$ is H; a $C_1$–$C_{12}$-alkyl, unsubstituted or substituted by phenyl, halophenyl or methylphenyl; or if $R^4$, $R^5$ and $R^6$=H, is amino, $C_1$–$C_4$ alkylamino, di-$C_1$–$C_4$-alkylamino, benzylamino, anilino, formylamino, $C_1$–$C_4$-alkylcarbonylamino, benzoylamino, hydroxyl, $C_1$–$C_6$-alkoxy or

in which Z=O, S or NH; the exceptions being those compounds in which $R^4$, $R^5$, $R^6$ and $R^7$=H;
$R^8$, $R^9$, $R^{10}$, $R^{11}$ independently of each other are $C_1$–$C_{18}$-alkyl, phenyl, unsubstituted or substituted by halogen, $C_1$–$C_4$-alkyl or $C_1$–$C_4$ alkoxy; or benzyl, unsubstituted or substituted by halogen, $C_1$–$C_4$ alkyl or $C_1$–$C_4$ alkoxy; and
$R^{12}$, $R^{13}$, $R^{14}$ independently of each other, are $C_1$–$C_6$-alkyl, phenyl, halophenyl, methylphenyl, benzyl, halobenzyl or methylbenzyl.

The alkyl, alkenyl and alkynyl radicals occurring in the general formula (I) as defined above, can be straight-chain or branched; halogen can be F, Cl, Br or I, in particular F, Cl or Br. Where the substituents $R^4$, $R^5$, $R^6$ and $R^7$ possess further basic nitrogen atoms, multiple salts formation is also possible; i.e. in such a case Y denotes only one cation equivalent, since a cation with several positive charges can neutralize several anions (in the present invention 1-phenylimidazole-5-carboxylate anions).

Another way of achieving the stated object is also the preparation of the compounds according to the invention from the corresponding free carboxylic acids or metal salts of the general formulae (II) and (III), Met+ denoting a metal cation with a single positive charge or a cation equivalent in the case of a metal cation with several positive charges, in particular where $Met^+$ = $Na^+$,

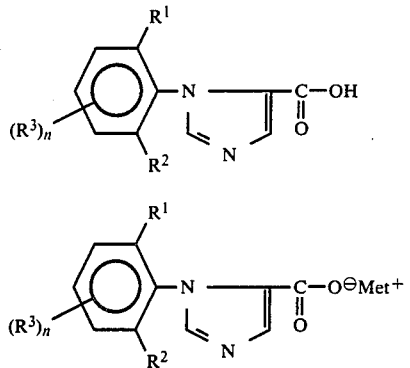

(a) by reacting (II) with the amino compounds Y' (Y'=minus H+) or with salts in which Y is a cation, wherein Y denotes

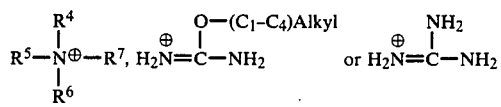

and at least one of the radicals $R^4$ to $R^7$ is H, or (b) by reacting (II) with compounds YHal− or YOH−, or reacting (III) with compounds YHal−, wherein Y is

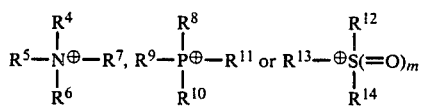

and all radicals $R^4$ to $R^7$ = H.

In variant (a) of the process, using the amine compounds Y' (i.e. Y'=Y minus H+), the use of equimolar amounts of the components is advantageous. In general, salt formation takes place straightforwardly, and can be carried out in the presence or absence of solvents such as water, alcohols, acetone, halogenated hydrocarbons, ethers, toluene, xylene or aliphatic or cycloaliphatic hydrocarbons. The solvent for the reaction should preferably be selected in such a way that the acid is sparingly soluble but the salt formed dissolves readily. The process of the reaction and the conversion of the components can then be readily observed by the dissolution of the precipitate. Suitable solvents of this type are for example water, ethanol, methanol, chloroform or methylene chloride. The reaction temperature is not critical; it is in general in the range from −20° C. to +100° C., in particular, however, between 0° C. and +50° C., at which temperature range salt formation is frequently weakly exothermic. The compounds according to the invention are obtained directly, when no solvents are used; when a solvent is used, it is recommended to distill it off for isolation of the products. In order to obtain the crude products in crystalline form, they can be, if desired, triturated with non-polar solvents (for example ether or hexane). The salts are then freed from the solvent by filtering them with suction; they are obtained in excellent yield and purity.

It is necessry for reasons, for example, of handling or stability, the amino compounds Y' can also be used in the form of salts (with Y as cation) and only converted to free bases Y' in the presence of the carboxylic acid of the general formula (II); examples of such salts are hydroxylammonium chloride, hydrochlorides of amino acid esters or hydrochlorides or sulfates of aminourea or thiourea. To this purpose, for example, the addition of propylene oxide or neutralization of the hydrohalides with stoichiometric amounts of inorganic bases such as the hydroxides, carbonates or bicarbonates of alkali or alkaline earth metals, may be used. The inorganic salts formed as byproducts can at the conclusion of the reaction be readily separated from the reaction mixture by dissolving the compounds prepared according to the invention in suitable solvents such as methylene chloride or acetone and filtering off the inorganic salts with suction. Further processing of the compounds according to the invention then takes place as described above.

If several amino groups are present, the corresponding mono-, di- or tri-salts can be prepared in a comparable manner by the addition of the corresponding mono-, di- or trimolar amounts of carboxylic acid of the general formula (II). Amine compounds Y' with several basic sites are for example hydrazine, ethylenediamine, propylenediamine, pyrazine or diethylenetriamine.

In the variant (b) of the process, in which the carboxylic acids of the general formula (II) are reacted with YHal− (ammonium, phosphonium, sulfonium or sulfoxonium halides) with separation of HHal (hydrogen halide), the addition of substances such as silver oxide or propylene oxide which under the reaction conditions react irreversibly with HHal, can be used to bring about the cleavage of HHal. The reaction is carried out preferably in water, methanol or ethanol. Isolation of the products takes place by evaporating the reaction mixture after separation of the byproducts (for example of silver halides by filtration, of halohydrins by extraction).

In the variant (b) of the process in which carboxlic acid of the general formula (II) is reacted with YOH− (ammonium, phosphonium, sulfonium or sulfoxonium hydroxides) with separation of $H_2O$, dehydrating agents such as molecular sieves can be added to the reaction mixture, or the water is advantageously removed by azeotropic distillation, using a suitable solvent such as toluene, benzene or chloroform.

In the variant (b) of the process in which the salts of carboxylic acids of the general formula (III) are reacted with YHal− with separation of Met+Hal− (metal halides), either the anhydrous metal carboxylate of the general formula (III) can be reacted with the halide, for example in an organic solvent such as toluene, xylene, chloroform, acetone or ethanol at a temperature between 20° C. and the boiling point of the solvent, the metal halide is being filtered off with suction at the end of the reaction and the product being isolated by evaporating the solvent, or the carboxylic acid of the general formula (II) is first reacted in water with the equivalent amount of an inorganic base such as hydroxides or carbonates of alkali metals to form the metal carboxylates of the general formula (III). This aqueous solution of the metal salt is then treated with the halide and the reaction mixture is heated to a temperature from 50° C. to 100° C. To isolate the desired product, the solvents are removed by distillation and the organic salt is freed from the inorganic salt by dissolution in an organic solvent.

The compounds according to the invention can be used to obtain typical growth-regulating effects which—compared with the compounds as well as salts known from DE-A No. 3,217,094—set in even at lower dosages (for example in a comparison with the structurally most comparable ammonium compound with $NH_4{}^+$ as the cation). They intervene in a regulatory manner in the metabolism of the plant and can therefore be used to exert a controlled influence on the plant constituents as well as for facilitating harvesting by say initiating drying out and stunted growth. They are also suitable for general control and inhibition of undesirable vegetative growth without at the same time killing off the plants. Inhibition of vegetative growth plays an important role for many lodging monocotyledon and dicotyledon crops, since lodging can be thereby reduced or fully prevented. Especially noteworthy is the growth-regulatory activity of the compounds as growth inhibitors in cereal, maize, soya bean, tobacco, cotton, tick beans, rape, rice and lawns, as well as the capability of the said compounds to increase the content of desired constituents such as carbohydrates (for example in sugarcane or millet crops) and protein in useful plants. Finally, the compounds give rise to greatly improved fruit separation, especially in citrus fruit.

Another way of achieving the stated object is plant growth regulators which are distinguished in that they contain an effective amount of at least one compound of the general formula (I). The rate of application of the compounds according to the invention is in general 0.02 to 1.5 kg of active substance per hectare, preferably 0.05 to 1 kg per hectare.

The compounds according to the invention may be, if desired and with advantage, combined in their practical application with known growth regulators. Plant growth regulators may then according to the invention additionally contain, besides at least one compound of the general formula (I), further active substances derived from chemically different groups of growth regulators. The preferred combined agents contain at least one compound of the general formula (I) in combination with a compound of the formula (IV), $$R-CH_2-CH_2-N^\ominus(CH_3)_3Cl \qquad (IV)$$

wherein

R denotes OH or Cl, or with a compound of the formula (V),

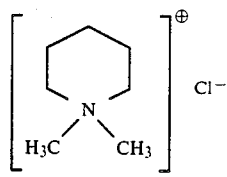
(V)

or with a compound of the formula (VI),

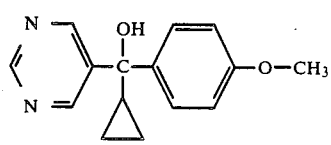
(VI)

or with a compound of the formula (VII),

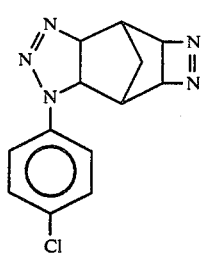
(VII)

or with a compound of the formula (VIII),

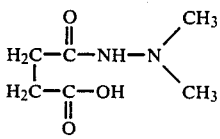
(VIII)

or with a compound of the formula (IX),

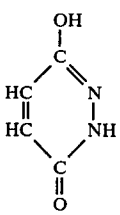
(IX)

or with a compound of the formula (X),

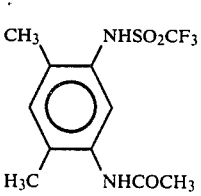
(X)

or with a compound of the formula (XI),

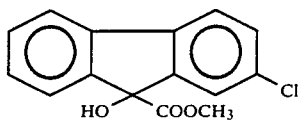

(XI)

or with a compound of the formula (XII)

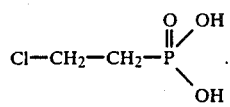

(XII)

The compounds of formulae (IV) to (XII) are known products commercially available. The compound of formula (IV) in which R=Cl [compound (IVa)] has the common name chlormequat. The compound of formula (V) is known as mepiquat chloride, the compound of formula (VI) as ancymidol, the compound of formula (VII) as tetcyclacis, the compound of formula (X) as mefluidid and the compound of formula (XII) as ethephon. The growth-regulatory activities of the compounds of formulae (IV) to (XII) are described in Plant Growth Regulator Handbook of the Plant Growth Regulator Working Group, 2nd ed., 1981.

Instead of the compounds of the formulae (VI) and (V), comparable salts can in principle also be used, which, instead of the chloride ion, contain another usual anion such as bromide, nitrate or ½ sulfate.

When the compounds of formula (I) are combined with the compounds of the formulae (IV) to (XII), surprisingly striking synergistic effects appear. Accordingly, these combinations can be used in even smaller doses than would be expected from the activities of the individual components, in order to achieve the desired effects. The combinations can also be used to reduce appearance of wild plant growth, so that the combinations can also be used in landscaping. In addition, these combinations are eminently suitable for general control and inhibition of undesirable vegetative growth, such as lateral shoot formation, without the plants being killed off. The compounds of formula (I) can also with advantage be combined with two different compounds of formulae (IV) to (XII).

The proportions of components of the general formula (I) in admixture with compounds of formulae (IV) to (XII) can vary within wide limits, between 250:1 and 1:10. The selection of the mixing ratio depends on the type of the components of the mixture, on the development stage of the plants as well as on the degree of desired growth-regulatory effect. The mixing ratio should be selected preferably from 10:1 to 1:10.

The rates of application of the compounds of formula (I) in the mixtures of active substances are in general between 0.05 and 1 kg of active substance per hectare, the rates of application of the compounds of formulae (IV) to (XII) vary between 0.01 and 5 kg of active substance per hectare. The combinations can be either in the form of mixed formulations of the individual components—for example as wettable powders or emulsion concentrates—which are then applied in the usual way diluted with water, or they can be produced as socalled tank mix by a joint dilution with water of the separately formulated components; there is also the possibility to apply the components consecutively, i.e. the components are applied as single-compound formulations.

Besides the active substances referred to above, i.e. in particular at least one compound of the general formula (I) and, if desired, an additional growth regulator, the agents according to the invention can also contain natural or plant hormones such as auxins or cytokinins.

The compounds according to the invention having the general formula (I) can be applied, in admixture with other active components if appropriate, as wettable powders, emulsifiable concentrates, sprayable solutions, dusts, dressings, dispersions, granules or microgranules in the customary formulations.

Wettable powders are preparations uniformly dispersible in water, which contain, besides the active substance or substances and, if desired, an extender or inert substance, a wetting agent such as polyoxyethylated fatty alcohols, alkyl- or alkylphenylsulfonates and/or dispersants such as sodium lignin-sulfonate, sodium 2,2'-dinaphthylmethane-6,6'-disulfonate, sodium dibutylnaphthalenesulfonate or sodium oleoylmethyltaurate. Preparation is carried out in the usual way, for example by grinding and mixing the components.

Emulsifiable concentrates can be prepared for example by dissolving the active substance or substances in an inert organic solvent such as butanol, cyclohexanone, dimethylformamide, xylene or higher boiling aromatics or aliphatic or cycloaliphatic hydrocarbons with the addition of one or more emulsifiers. For liquid active substances, the solvent portion can be totally or partially omitted. Examples of emulsifiers which can be used are calcium salts of alkylarylsulfonates such as calcium dodecyl-benzenesulfonate or non-ionic emulsifiers such as polyglycol esters of fatty acids, alkylaryl polyglycol ethers, polyglycol ethers of fatty alcohols, propylene oxide/ethylene oxide condensation products, fatty alcohol/propylene oxide condensation products, alkyl polyglycol ethers, sorbitol fatty acid esters, polyoxyethylenesorbitan fatty acid esters or polyoxyethylenesorbitol esters.

Dusts are obtained by grinding of the active substance or substances with finely divided solids, for example talc, natural clays such as kaolin, bentonite, pyrophyllite or diatomaceous earth. Granules can be prepared either by spraying the active substance or substances onto granular inert adsorbants or by applying active substance concentrates onto the surface of carriers such as sand, kaolinites or granular inert material with the aid of binders, for example polyvinyl alcohol, sodium polyacrylate as well as mineral oils. Suitable active substances can also be granulated by the method usually used for the preparation of granular fertilizers—in admixture with fertilizers if appropriate.

The concentration of the active substance in wettable powders is about 10 to 90% by weight, the remainder to 100% by weight consisting of the usual formulation constituents. Active substance concentration in emulsifiable concentrates can amount to approximately 10 to 80% by weight. Dust formulations usually contain 5 to 20% by weight of active substance or substances, sprayable solutions about 2 to 20% by weight. The active substance content in granules will partly depend on whether the active compound is a liquid or a solid and which granulation aids, fillers etc. are being used. In addition the active substance formulations, already referred to, contain, if appropriate, the usual adhesives, wetting agents, dispersants, emulsifiers, penetrants, solvents, fillers or carriers.

For application, the commercially available forms of concentrates are diluted in the usual manner as appropriate, for example in the case of wettable powders, emulsifiable concentrates, dispersions and in part also microgranules, with water. Preparations in the form of dusts or granules as well as sprayable solutions are usually not further diluted by inert substances before application.

Mixtures or mixed formulations with other active substances such as insecticides, acaricides, herbicides, fertilizers or fungicides are also possible, as appropriate.

In the examples which follow, parts by weight (pbw) relate to parts by volume (pbv) as kg to dm$^3$ (l), and % data refer to percentage by weight, unless otherwise indicated.

FORMULATION EXAMPLES

Example 1

A dusting agent is obtained when (a) 10 pbw of the active substance or substances and 90 pbw of talc or another inert substance are mixed and comminuted in a hammer mill, or when (b) 60 pbw of the active substance, 35 pbw of talc and 5 pbw of an adhesive (for example a polysaccharide such as Rhodopol® from Rhone-Poulenc S.A.) are homogenized in the same manner.

Example 2

A wettable powder, readily dispersible in water, is obtained when 25 pbw of the active substance or substances, 64 pbw of a kaolin-containing quartz as inert substance, 10 pbw of potassium ligninsulfonate and 1 pbw of sodium oleoylmethyltaurate as wetting agent and dispersant are mixed and ground in a pinned disk mill. A formulation containing 5% active substance, can have the following composition: 5% of active substance or substances, 6% of a sulfonated naphthalene/formaldehyde condensate (for example Dispersogen A® from HOECHST AG), 2% of a sodium alkylnaphthalenesulfonate (for example Leonil DB® from HOECHST AG), 5% of a mixture of polypropylene glycol and SiO$_2$ (for example Acrotin 341® from HOECHST AG), 25% of SiO$_2$ (for example Sipernat® from Degussa AG) and 57% of kaolin type 1777.

Example 3

A dispersion concentrate, readily dispersible in water, is obtained when 20 pbw of the active substance or substances are mixed with 6 pbw of an alkylphenol polyglycol ether (for example Triton X 207® from Rohm and Haas Co.), 3 pbw of isotridecanol polyglycol ether (8 ethylene oxide units) and 71 pbw of a paraffinic mineral oil (boiling range from about 225° to above 377° C.) and the mixture is ground in a frictional ball mill to a particle size of less than 5 μm.

Example 4

An emulsifiable concentrate is obtained from 15 pbw of the active substance or substances, 75 pbw of cyclohexanone as solvent and 10 pbw of oxyethylated nonylphenol (10 ethylene oxide units) as emulsifier.

CHEMICAL EXAMPLES

Example 1

Methylammonium 1-(2,6-diethylphenyl)imidazole-5-carboxylate 5.7 pbw (0.073 mole) of a 40% aqueous solution of methylamine are added dropwise to 15 pbw (0.061 mole) of 1-(2,6-diethylphenyl)imidazole-5-carboxylic acid in 50 pbv of methylene chloride. After 2 hours the mixture is evaporated in vacuo, the residue is stirred with 100 pbv of diethyl ether and filtered off with suction. 15.7 pbw (93% of theory) of methylammonium 1-(2,6-diethylphenyl)imidazole-5-carboxylate, a colorless solid with a m.p. of 110°–113° C., are obtained.

Example 2

Ethoxycarbonylmethylammoninum 1-(2,6-diethylphenyl)imidazole-5-carboxylate 14.9 pbw (0.25 mole) of propylene oxide are added dropwise to 25 pbw (0.10 mole) of 1-(2,6-diethylphenyl)imidazole-5-carboxylic acid, 15.7 pbw (0.11 mole) of ethyl glycinate hydrochloride and 50 pbv of methylene chloride. After 2 hours heating under reflux, a clear solution has formed. It is allowed to cool and is evaporated. The residual oil is digested with twice 100 pbv of diethyl ether and dried. 22.8 pbw (63% of theory) of ethoxycarbonylmethylammonium 1-(2,6-diethylphenyl)imidazole-5-carboxylate, a colorless, high-viscosity oil, are obtained; identification is carried out by $^1$H-NMR spectroscopy.

Example 3

2-Hydroxyethyltrimethylammonium 1-(2,6-diethylphenyl)imidazole-5-carboxylate 25 pbw (0.10 mole) of 1-(2,6-diethylphenyl)imidazole-5-carboxylic acid and 27.0 pbw (0.11 mole) of a 50% aqueous solution of choline are heated in 100 pbv of toluene in a water separator, until the water has been completely removed. The mixture is allowed to cool and is then evaporated in vacuo. 34.5 pbw (97% of theory) of 2-hydroxyethyltrimethylammonium 1-(2,6-diethylphenyl)imidazole-5-carboxylate, a high-viscosity oil, are obtained; identification is carried out by $^1$H-NMR spectroscopy.

Example 4

Tetraethylammonium 1-(2,6-diethylphenyl)imidazole-5-carboxylte 15 pbw (0.061 mole) of 1-(2,6-diethylphenyl)imidazole-5-carboxylic acid are stirred with 14.0 pbw (0.067 mole) of tetraethylammonium bromide and 4.5 pbw (0.078 mole) of propylene oxide in 50 pbv of water for 24 hours at room temperature. The then homogeneous phase is washed twice with diethyl ether and the aqueous phase is evaporated. 20.4 pbw (89% of theory) of tetraethylammonium 1-(2,6-diethylphenyl)imidazole-5-carboxylate, a viscous oil, are obtained; identification is carried out by $^1$H-NMR spectroscopy.

Example 5

2-Chloroethyltrimethylammonium 1-(2,6-diethylphenyl)imidazole-5-carboxylate 15 pbw (0.061 mole) of 1-(2,6-diethylphenyl)imidazole-5-carboxylic acid are stirred with 10.2 pbw (0.064 mole) of choline dichloride and 5.5 pbw (0.065 mole) of sodium bicarbonate in 50 pbv of water for 8 hours at 50° C. At the end of this period a homogeneous solution forms; it is evaporated, taken up in 200 pbv of methylene chloride, and is evaporated after removal of the inorganic salts by filtration. 19.6 pbw (87% of theory) of 2-chloroethyltrimethylammonium 1-(2,6-diethylphenyl)imidazole-5-carboxylate, a viscous oil, are obtained; identification is carried out by $^1$H-NMR spectroscopy.

The substances listed in Table 1 are prepared on the basis of the foregoing examples.

TABLE 1

Compounds of formula (I)

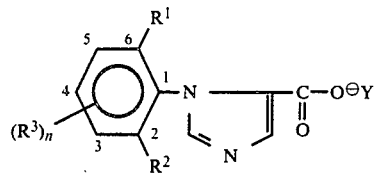

(I)

| Example No. | $R^1$ | $R^2$ | $R^3$/n | Y | Prepared according to Example | M.p. (°C.) |
|---|---|---|---|---|---|---|
| 6 | $CH_3$ | $CH_3$ | —/0 | $H_2\overset{\oplus}{N}$—$(CH(CH_3)_2)_2$ | 1 | |
| 7 | $CH_3$ | $CH_3$ | —/0 | $H_2\overset{\oplus}{N}(\text{—}CH(CH_3)_2)\text{—}\bigcirc\text{—}H$ | 1 | |
| 8 | $CH_3$ | $CH_3$ | 4-$CH_3$/1 | $(C_4H_9)_3\overset{\oplus}{P}$—$C_{18}H_{37}$ | 4 | |
| 9 | $CH_3$ | $CH_3$ | 4-$CH_3$/1 | $(C_4H_9)_3\overset{\oplus}{P}$—$C_{16}H_{33}$ | 4 | |
| 10 | $CH_2$ | $C_2H_5$ | 5-$CH_3$/1 | $H_3\overset{\oplus}{N}$—$CH_2$—$\bigcirc$—H | 1 | ° |
| 11 | $C_2H_5$ | $C_2H_5$ | —/0 | $H_2\overset{\oplus}{N}(\text{—}CH_3)_2$ | 1 | 78–80 |
| 12 | $C_2H_5$ | $C_2H_5$ | —/0 | $H\overset{\oplus}{N}(\text{—}CH_3)_3$ | 1 | Resin |
| 13 | $C_2H_5$ | $C_2H_5$ | —/0 | $H_3\overset{\oplus}{N}$—$C_2H_5$ | 1 | 72–8 |
| 14 | $C_2H_5$ | $C_2H_5$ | —/0 | $H\overset{\oplus}{N}(\text{—}C_2H_5)_3$ | 1 | 130–5 |
| 15 | $C_2H_5$ | $C_2H_5$ | —/0 | $H_3\overset{\oplus}{N}$—$CH(CH_3)_2$ | 1 | 144–5 |
| 16 | $C_2H_5$ | $C_2H_5$ | —/0 | $H_3\overset{\oplus}{N}$—$C_4H_9$ | 1 | 149–56 |
| 17 | $C_2H_5$ | $C_2H_5$ | —/0 | $H_2\overset{\oplus}{N}(\text{—}C_4H_9)_2$ | 1 | 147–54 |
| 18 | $C_2H_5$ | $C_2H_5$ | —/0 | $H\overset{\oplus}{N}(\text{—}C_4H_9)_3$ | 1 | 108–14 |
| 19 | $C_2H_5$ | $C_2H_5$ | —/0 | $H_3\overset{\oplus}{N}(\text{—}CH_2)_2$—$CH(CH_3)_2$ | 1 | 135–42 |
| 20 | $C_2H_5$ | $C_2H_5$ | —/0 | $H_3\overset{\oplus}{N}$—n-$C_{12}H_{25}$ | 1 | |
| 21 | $C_2H_5$ | $C_2H_5$ | —/0 | $H_3\overset{\oplus}{N}$—n-$C_{18}H_{37}$ | 1 | Wax |
| 22 | $C_2H_5$ | $C_2H_5$ | —/0 | $H_2\overset{\oplus}{N}$—n-$(C_{18}H_{37})_2$ | 1 | Wax |
| 23 | $C_2H_5$ | $C_2H_5$ | —/0 | $H_3\overset{\oplus}{N}$—$CH_2$—$CH_2$—$OCH_3$ | 1 | 121–3 |

TABLE 1-continued

Compounds of formula (I)

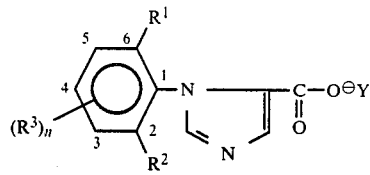

| Example No. | R¹ | R² | R³/n | Y | Prepared according to Example | M.p. (°C.) |
|---|---|---|---|---|---|---|
| 24 | $C_2H_5$ | $C_2H_5$ | —/0 | $\overset{\oplus}{H_3N}-CH_2-CH(OCH_3)_2$ | 1 | 114–62 |
| 25 | $C_2H_5$ | $C_2H_5$ | —/0 | $\overset{\oplus}{H_3N}(-CH_2)_3-O-CH_3$ | 1 | 153–6 |
| 26 | $C_2H_5$ | $C_2H_5$ | —/0 | $\overset{\oplus}{H_3N}(-CH_2)_3-O-CH(CH_3)_2$ | 1 | 133–4 |
| 27 | $C_2H_5$ | $C_2H_5$ | —/0 | $\overset{\oplus}{H_3N}-CH_2-$ (dimethylbicyclic group) | 1 | 160–1 |
| 28 | $C_2H_5$ | $C_2H_5$ | —/0 | $\overset{\oplus}{H_3N}-CH_2-CH_2-$ (dimethylbicyclic group) | 1 | 206–10 |
| 29 | $C_2H_5$ | $C_2H_5$ | —/0 | $\overset{\oplus}{H_3N}-CH_2-$ phenyl | 1 | 171–4 |
| 30 | $C_2H_5$ | $C_2H_5$ | —/0 | $\overset{\oplus}{H_3N}-CH_2-CN$ | 2 | |
| 31 | $C_2H_5$ | $C_2H_5$ | —/0 | $\overset{\oplus}{H_3N}-CH_2-CH_2-OH$ | 1 | 108–16 |
| 32 | $C_2H_5$ | $C_2H_5$ | —/0 | $\overset{\oplus}{H_2N}(-CH_2-CH_2-OH)_2$ | 1 | 141–9 |
| 33 | $C_2H_5$ | $C_2H_5$ | —/0 | $\overset{\oplus}{HN}(-CH_2-CH_2-OH)_3$ | 1 | 83–8 |
| 34 | $C_2H_5$ | $C_2H_5$ | —/0 | $(CH_3-)_2\overset{\oplus}{NH}-CH_2-CH_2-OH$ | 1 | 119–21 |
| 35 | $C_2H_5$ | $C_2H_5$ | —/0 | $\overset{\oplus}{H_3N}-CH_2-CH(OH)-CH_3$ | 1 | 102–14 |
| 36 | $C_2H_5$ | $C_2H_5$ | —/0 | $\overset{\oplus}{H_3N}-C(CH_3)_2-CH(OH)-CH_3$ | 1 | 80–4 |
| 37 | $C_2H_5$ | $C_2H_5$ | —/0 | $(CH_3-)_2\overset{\oplus}{NH}(-CH_2)_3-OH$ | 1 | 134–8 |
| 38 | $C_2H_5$ | $C_2H_5$ | —/0 | $\overset{\oplus}{H_3N}-CH(CH_3)-COOCH_3$ | 2 | Oil |
| 39 | $C_2H_5$ | $C_2H_5$ | —/0 | $\overset{\oplus}{H_3N}-CH_2-COOCH_3$ | 1 | 140–54 (decomp) |
| 40 | $C_2H_5$ | $C_2H_5$ | —/0 | $\overset{\oplus}{H_3N}-\underset{CONH_2}{C(CH_3)}-CH(CH_3)_2$ | 1 | |
| 41 | $C_2H_5$ | $C_2H_5$ | —/0 | $\overset{\oplus}{H_3N}-CH_2-CH_2-NH_2$ | 1 | |

TABLE 1-continued

Compounds of formula (I)

$$\text{(I)}$$

(Structure: phenyl ring with positions labeled 1-6, R¹ at 6, R² at 2, (R³)ₙ at 3/4/5, N attached at 1 connecting to imidazole ring with C-O⁻Y group)

| Example No. | R¹ | R² | R³/n | Y | Prepared according to Example | M.p. (°C.) |
|---|---|---|---|---|---|---|
| 42 | $C_2H_5$ | $C_2H_5$ | —/0 | $\frac{1}{2}\cdot(\overset{\oplus}{H_3N}-CH_2-CH_2-\overset{\oplus}{NH_3})$ | 1 | 185–95 |
| 43 | $C_2H_5$ | $C_2H_5$ | —/0 | $\overset{\oplus}{H_2N}(-CH_2-CH_2-NH_2)_2$ | 1 | |
| 44 | $C_2H_5$ | $C_2H_5$ | —/0 | $(CH_3-)_2\overset{\oplus}{NH}-CH_2-CH_2-N(CH_3)_2$ | 1 | |
| 45 | $C_2H_5$ | $C_2H_5$ | —/0 | $\overset{\oplus}{H_3N}-CH_2-CH=CH_2$ | 1 | |
| 46 | $C_2H_5$ | $C_2H_5$ | —/0 | $\overset{\oplus}{H_2N}(-CH_2-CH=CH_2)_2$ | 1 | |
| 47 | $C_2H_5$ | $C_2H_5$ | —/0 | $\overset{\oplus}{H_3N}$-cyclopropyl | 1 | |
| 48 | $C_2H_5$ | $C_2H_5$ | —/0 | $\overset{\oplus}{H_3N}$-cyclohexyl (H) | 1 | 172–4 |
| 49 | $C_2H_5$ | $C_2H_5$ | —/0 | $\overset{\oplus}{H_3N}$-(2-isopropyl-5-methylcyclohexyl) | 1 | Resin |
| 50 | $C_2H_5$ | $C_2H_5$ | —/0 | $\overset{\oplus}{H_2N}$-cyclooctyl | 1 | |
| 51 | $C_2H_5$ | $C_2H_5$ | —/0 | $(CH_3-)_2\overset{\oplus}{NH}$-phenyl | 1 | |
| 52 | $C_2H_5$ | $C_2H_5$ | —/0 | $\overset{\oplus}{H_2N}$-pyrrolidinyl | 1 | 173–6 |
| 53 | $C_2H_5$ | $C_2H_5$ | —/0 | $\overset{\oplus}{H_2N}$-piperidinyl | 1 | 174–7 |
| 54 | $C_2H_5$ | $C_2H_5$ | —/0 | $\overset{\oplus}{H_2N}$-(3-methylpiperidinyl) | 1 | 187–90 |

TABLE 1-continued

Compounds of formula (I)

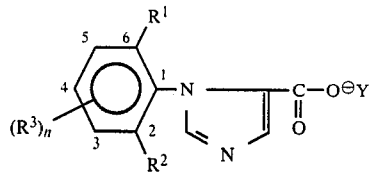

| Example No. | R¹ | R² | R³/n | Y | Prepared according to Example | M.p. (°C.) |
|---|---|---|---|---|---|---|
| 55 | $C_2H_5$ | $C_2H_5$ | —/0 | 4-tert-butyl-piperidinium | 1 | Resin |
| 56 | $C_2H_5$ | $C_2H_5$ | —/0 | $HO-CH_2-CH_2-\overset{\oplus}{N}H$-piperidine | 1 | Resin |
| 57 | $C_2H_5$ | $C_2H_5$ | —/0 | 2,2,6,6-tetramethyl-4-oxo-piperidinium | 1 | 153 Resin |
| 58 | $C_2H_5$ | $C_2H_5$ | —/0 | 4-amino-2,2,6,6-tetramethyl-piperidinium | 1 | 204–7 |
| 59 | $C_2H_5$ | $C_2H_5$ | —/0 | azocanium ($H_2\overset{\oplus}{N}$-ring) | 1 | 100–2 |
| 60 | $C_2H_5$ | $C_2H_5$ | —/0 | 3,3,5-trimethyl-hexahydroazepinium | 1 | 118–26 (decomp) |
| 61 | $C_2H_5$ | $C_2H_5$ | —/0 | $[H-(HN\text{---}N)]^{\oplus}$ imidazolium | 1 | |
| 62 | $C_2H_5$ | $C_2H_5$ | —/0 | $H_2\overset{\oplus}{N}$-piperazine-NH | 1 | |
| 63 | $C_2H_5$ | $C_2H_5$ | —/0 | ½($H_2\overset{\oplus}{N}$-piperazine-$\overset{\oplus}{N}H_2$) | 1 | |
| 64 | $C_2H_5$ | $C_2H_5$ | —/0 | $H_2\overset{\oplus}{N}$-piperazine-$N-CH_3$ | 1 | 102–7 |

TABLE 1-continued

Compounds of formula (I)

$$\text{(I)}$$

(Structure: phenyl ring with positions 1-6, substituents $R^1$ at 6, $R^2$ at 2, $(R^3)_n$ at 3/4/5; N at position 1 connected to imidazole ring bearing —C(=O)—O$^\ominus$Y)

| Example No. | $R^1$ | $R^2$ | $R^3/n$ | Y | Prepared according to Example | M.p. (°C.) |
|---|---|---|---|---|---|---|
| 65 | $C_2H_5$ | $C_2H_5$ | —/0 | $H_2\overset{\oplus}{N}$–piperazine–$N$–$CH_2$–phenyl | 1 | |
| 66 | $C_2H_5$ | $C_2H_5$ | —/0 | $H_2\overset{\oplus}{N}$–morpholine | 1 | Oil |
| 67 | $C_2H_5$ | $C_2H_5$ | —/0 | $H_2\overset{\oplus}{N}$–(2,6-dimethylmorpholine) | 1 | 101–7 |
| 68 | $C_2H_5$ | $C_2H_5$ | —/0 | HO—$CH_2$—$CH_2$—$\overset{\oplus}{\underset{H}{N}}$–morpholine | 1 | Oil |
| 69 | $C_2H_5$ | $C_2H_5$ | —/0 | $\overset{\oplus}{N}(-C_4H_9)_4$ | 4 | Resin |
| 70 | $C_2H_5$ | $C_2H_5$ | —/0 | phenyl–$CH_2$–$\overset{\oplus}{N}(-C_2H_5)_3$ | 4 | Oil |
| 71 | $C_2H_5$ | $C_2H_5$ | —/0 | $(CH_3-)_3\overset{\oplus}{N}-C_8H_{17}$ | 4 | |
| 72 | $C_2H_5$ | $C_2H_5$ | —/0 | $(C_2H_5-)_3\overset{\oplus}{N}-C_{12}H_{25}$ | 4 | |
| 73 | $C_2H_5$ | $C_2H_5$ | —/0 | $H_3\overset{\oplus}{N}-NH_2$ | 1 | |
| 74 | $C_2H_5$ | $C_2H_5$ | —/0 | $\tfrac{1}{2}\cdot(H_3\overset{\oplus}{N}-\overset{\oplus}{N}H_3)$ | 1 | 135–40 |
| 75 | $C_2H_5$ | $C_2H_5$ | —/0 | $H_3\overset{\oplus}{N}-NHCHO$ | 1 | 123–9 |
| 76 | $C_2H_5$ | $C_2H_5$ | —/0 | $H_3\overset{\oplus}{N}-NH-\text{Phenyl}$ | 1 | |
| 77 | $C_2H_5$ | $C_2H_5$ | —/0 | $H_3\overset{\oplus}{N}-OH$ | 2 | Oil |
| 78 | $C_2H_5$ | $C_2H_5$ | —/0 | $H_3\overset{\oplus}{N}-OCH_3$ | 2 | Oil |
| 79 | $C_2H_5$ | $C_2H_5$ | —/0 | $H_3\overset{\oplus}{N}-NH-(C=NH)NH_2$ | 2 | 100–2 |
| 80 | $C_2H_5$ | $C_2H_5$ | —/0 | $H_3\overset{\oplus}{N}-NH-CS-NH_2$ | 2 | |
| 81 | $C_2H_5$ | $C_2H_5$ | —/0 | $[H-(H_2N-\overset{NH}{\underset{\parallel}{C}}-NH_2)]^{\oplus}$ | 2 | 193–4 |

TABLE 1-continued

Compounds of formula (I)

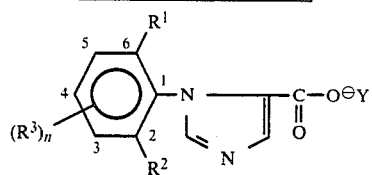

| Example No. | $R^1$ | $R^2$ | $R^3/n$ | Y | Prepared according to Example | M.p. (°C.) |
|---|---|---|---|---|---|---|
| 82 | $C_2H_5$ | $C_2H_5$ | —/0 | $CH_3-\overset{\oplus}{P}(-C_4H_9)_3$ | 4 | Resin |
| 83 | $C_2H_5$ | $C_2H_5$ | —/0 | $\overset{\oplus}{P}(-C_4H_9)_4$ | 4 | |
| 84 | $C_2H_5$ | $C_2H_5$ | —/0 | $\overset{\oplus}{P}(-C_8H_{17})_4$ | 4 | |
| 85 | $C_2H_5$ | $C_2H_5$ | —/0 | $CH_3-\overset{\oplus}{P}(-Phenyl)_3$ | 4 | |
| 86 | $C_2H_5$ | $C_2H_5$ | —/0 | $\overset{\oplus}{P}(-Phenyl)_4$ | 4 | |
| 87 | $C_2H_5$ | $C_2H_5$ | —/0 | $\overset{\oplus}{S}(-CH_3)_3$ | 4,5 | Resin |
| 88 | $C_2H_5$ | $C_2H_5$ | —/0 | $O-\overset{\oplus}{S}(-CH_3)_3$ | 4 | 134–43 |
| 89 | $C_2H_5$ | $C_2H_5$ | —/0 | $\overset{\oplus}{S}(-CH_3)_2-CH_2-Phenyl$ | 4 | |
| 90 | $C_2H_5$ | $C_2H_5$ | 4-Br/1 | $\overset{\oplus}{H_2N}\langle\text{piperidine}\rangle$ | 1 | 135–8 |
| 91 | $C_2H_5$ | $C_2H_5$ | 4-Br/1 | $\overset{\oplus}{H_2N}\langle\text{piperazine}\rangle N-Phenyl$ | 1 | |
| 92 | $C_2H_5$ | $C_2H_5$ | 4-Br/1 | $\overset{\oplus}{H_3N}-N(CH_3)_2$ | 1 | |
| 93 | $C_2H_5$ | $CH(CH_3)_2$ | —/0 | $\overset{\oplus}{H_2N}(-C_2H_5)_2$ | 1 | |
| 94 | $C_2H_5$ | $CH(CH_3)_2$ | —/0 | $\overset{\oplus}{H_3N}-n-C_3H_7$ | 1 | |
| 95 | $C_2H_5$ | $CH(CH_3)_2$ | —/0 | $\overset{\oplus}{H_2N}-n-(C_{18}H_{37})_2$ | 1 | Wax |
| 96 | $C_2H_5$ | $CH(CH_3)_2$ | —/0 | $\overset{\oplus}{H_3N}(-CH_2)_2-O-(CH_2)_2-OCH_3$ | 1 | |
| 97 | $C_2H_5$ | $CH(CH_3)_2$ | —/0 | $\overset{\oplus}{H_3N}(-CH_2)_2-O-CH_2-Phenyl$ | 1 | |
| 98 | $CH(CH_3)_2$ | $CH(CH_3)_2$ | —/0 | $\overset{\oplus}{H_3N}-CH_2-COOH$ | 1 | |
| 99 | $CH(CH_3)_2$ | $CH(CH_3)_2$ | —/0 | $\overset{\oplus}{H_3N}-NH-CONH_2$ | 2 | |
| 100 | $CH(CH_3)_2$ | $CH(CH_3)_2$ | —/0 | $CH_3-\overset{\oplus}{NH}-CH(CH_3)-CH(OH)-Phenyl$ | 1 | |
| 101 | $CH(CH_3)_2$ | $CH(CH_3)_2$ | —/0 | $\overset{\oplus}{H_3N}-C(CH_3)_3$ | 1 | |

TABLE 1-continued

Compounds of formula (I)

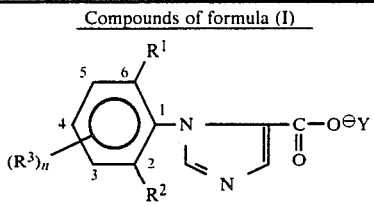

| Example No. | R¹ | R² | R³/n | Y | Prepared according to Example | M.p. (°C.) |
|---|---|---|---|---|---|---|
| 102 | CH(CH₃)₂ | CH(CH₃)₂ | —/0 | $\overset{\oplus}{H_2N}$⟨ ⟩—OH | 1 | |
| 103 | CH(CH₃)₂ | CH(CH₃)₂ | —/0 | $\overset{\oplus}{H_2N}$⟨ ⟩—CH₂—CH₂—OH | 1 | |
| 104 | CH(CH₃)₂ | CH(CH₃)₂ | —/0 | $\overset{\oplus}{HN}$(—CH₂—CH(OH)—CH₃)₃ | 1 | |
| 105 | CH₃ | CH(CH₃)₂ | —/0 | $\overset{\oplus}{HN}$(—CH₂—CH₂—OH)₃ | 1 | Resin |
| 106 | C₂H₅ | C₂H₅ | —/0 | $\overset{\oplus}{H_3N}$—C(CH₃)₂—CH₂OH | 1 | 152–8 |
| 107 | C₂H₅ | C₂H₅ | —/0 | $(CH_3)_2\overset{\oplus}{NH}$—CH₂—CH₂—CN | 1 | 100–3 |
| 108 | C₂H₅ | C₂H₅ | —/0 | [H(H₂N—C(=NH)—NH(CH₂)₃—CH(NH₂)COOH)]⊕ | 1 | 72–5 |
| 109 | C₂H₅ | C₂H₅ | —/0 | $\overset{\oplus}{H_3N}$—C(CN)(CH₃)—CH(CH₃)₂ | 1 | 142–52 |
| 110 | C₂H₅ | C₂H₅ | —/0 | $(CH_3)_3C—\overset{\oplus}{NH}$(—CH₂—CH₂—OH)₂ | 1 | 150–2 |
| 111 | C₂H₅ | C₂H₅ | 4-CH₃/1 | $\overset{\oplus}{H_2N}$⟨ ⟩ | 1 | 168–72 |
| 112 | C₂H₅ | C₂H₅ | 4-CH₃/1 | $\overset{\oplus}{HN}$(—CH₂—CH₂—OH)₃ | 1 | 67–9 |
| 113 | C₂H₅ | C₂H₅ | 3-CH₃/1 | $\overset{\oplus}{H_2N}$⟨ ⟩ | 1 | 119–22 |
| 114 | C₂H₅ | C₂H₅ | 3-CH₃/1 | HN(—CH₂—CH₂—OH)₃ | 1 | 54–8 |

BIOLOGICAL EXAMPLES

1. Growth inhibition of cereals

In experiments in the greenhouse, young cereal plants in trays (wheat, barley, rye) in the 3-leaf stage are sprayed with the compounds according to the invention in various active substance concentrations (kg/ha) until dripping wet.

When the untreated control plants have grown to a height of about 55 cm, the growth of all the plants is measured and the growth inhibition is calculated in % of the growth of the control plants. The phytotoxic activity of the compound is also observed. Growth inhibition is expressed as a percentage, 100% denoting growth that has halted and 0% denoting a growth corresponding to that of the untreated control plants.

TABLE I

| Compound of Ex.No. | dosage (kg/ha) | growth inhibition (%) | | | phytotoxicity |
|---|---|---|---|---|---|
| 1 | 2.5 | 22 | 40 | 29 | no |
|  | 1.25 | 17 | 21 | 20 | damages |
| 2 | 2.5 | 22 | 39 | 28 | no |
|  | 1.25 | 17 | 20 | 19 | damages |
| 3 | 2.5 | 20 | 37 | 27 | no |
|  | 1.25 | 15 | 17 | 16 | damages |
| 4 | 2.5 | 21 | 36 | 26 | no |

TABLE I-continued

| Compound of Ex.No. | dosage (kg/ha) | growth inhibition (%) | | | phyto-toxicity |
|---|---|---|---|---|---|
| 17 | 1.25 | 14 | 17 | 17 | damages |
|  | 2.5 | 22 | 40 | 28 | no |
| 18 | 1.25 | 17 | 22 | 21 | damages |
|  | 2.5 | 21 | 39 | 27 | no |
| 19 | 1.25 | 16 | 20 | 19 | damages |
|  | 2.5 | 21 | 39 | 28 | no |
| 21 | 1.25 | 17 | 21 | 17 | damages |
|  | 2.5 | 20 | 36 | 27 | no |
| 24 | 1.25 | 16 | 20 | 19 | damages |
|  | 2.5 | 21 | 39 | 28 | no |
| 25 | 1.25 | 17 | 17 | 19 | damages |
|  | 2.5 | 21 | 38 | 27 | no |
| 27 | 1.25 | 16 | 17 | 18 | damages |
|  | 2.5 | 22 | 39 | 28 | no |
| 29 | 1.25 | 17 | 16 | 20 | damages |
|  | 2.5 | 21 | 39 | 29 | no |
| 33 | 1.25 | 16 | 17 | 19 | damages |
|  | 2.5 | 21 | 38 | 29 | no |
| 34 | 1.25 | 17 | 18 | 19 | damages |
|  | 2.5 | 21 | 37 | 29 | no |
| 40 | 1.25 | 17 | 17 | 18 | damages |
|  | 2.5 | 20 | 36 | 27 | no |
| 42 | 1.25 | 16 | 15 | 18 | damages |
|  | 2.5 | 21 | 38 | 28 | no |
| 49 | 1.25 | 17 | 17 | 19 | damages |
|  | 2.5 | 21 | 39 | 29 | no |
| 52 | 1.25 | 17 | 17 | 20 | damages |
|  | 2.5 | 21 | 36 | 26 | no |
| 53 | 1.25 | 15 | 17 | 17 | damages |
|  | 2.5 | 21 | 39 | 26 | no |
| 54 | 1.25 | 17 | 19 | 20 | damages |
|  | 2.5 | 21 | 39 | 29 | no |
| 58 | 1.25 | 17 | 16 | 20 | damages |
|  | 2.5 | 20 | 36 | 27 | no |
| 59 | 1.25 | 15 | 16 | 19 | damages |
|  | 2.5 | 21 | 38 | 28 | no |
| 64 | 1.25 | 17 | 18 | 20 | damages |
|  | 2.5 | 21 | 38 | 27 | no |
| 67 | 1.25 | 17 | 19 | 18 | damages |
|  | 2.5 | 21 | 36 | 28 | no |
| 68 | 1.25 | 17 | 18 | 19 | damages |
|  | 2.5 | 20 | 37 | 26 | no |
| 73 | 1.25 | 15 | 16 | 17 | damages |
|  | 2.5 | 20 | 37 | 29 | no |
| 75 | 1.25 | 15 | 16 | 18 | damages |
|  | 2.5 | 21 | 38 | 27 | no |
| 77 | 1.25 | 16 | 17 | 18 | damages |
|  | 2.5 | 22 | 37 | 27 | no |
| 79 | 1.25 | 16 | 19 | 18 | damages |
|  | 2.5 | 21 | 37 | 29 | no |
| 81 | 1.25 | 17 | 19 | 21 | damages |
|  | 2.5 | 22 | 35 | 27 | no |
| 82 | 1.25 | 16 | 18 | 18 | damages |
|  | 2.5 | 21 | 35 | 27 | no |
| 88 | 1.25 | 16 | 14 | 18 | damages |
|  | 2.5 | 21 | 36 | 29 | no |
| 90 | 1.25 | 16 | 21 | 16 | damages |
|  | 2.5 | 21 | 39 | 29 | no |
| 105 | 1.25 | 17 | 17 | 18 | damages |
|  | 2.5 | 21 | 36 | 26 | no |
| 108 | 1.25 | 15 | 18 | 17 | damages |
|  | 2.5 | 21 | 35 | 27 | no |
| 109 | 1.25 | 16 | 16 | 19 | damages |
|  | 2.5 | 24 | 41 | 26 | no |
| 111 | 1.25 | 19 | 21 | 19 | damages |
|  | 2.5 | 21 | 37 | 25 | no |
| 114 | 1.25 | 17 | 21 | 17 | damages |
|  | 2.5 | 22 | 36 | 25 | no |
| CCC | 1.25 | 17 | 18 | 16 | damages |
|  | 2.5 | 27 | 8 | 10 | no |
|  | 1.25 | 23 | 0 | 0 | damages |

CCC = 2-Chlorethyltrimethylammoniumchloride

2. Growth inhibition of water rice

Rice plants grown in small plots (2 m×2 m) are treated in the stage of maximum side shoot growth with the compounds according to the invention. The substances are applied both by spraying and by introduction into the water.

3 weeks after treatment, the growth of all the plants is measured and the growth inhibition is calculated as a percentage of the growth of the control plants. Attention is also paid as to whether there is any phytotoxic activity of the compounds. Growth inhibition is expressed as a percentage, 100% denoting that growth has halted and 0% denoting a growth corresponding to that of the untreated control plants.

TABLE II

| Compound of Ex. No. | dosage (kg/ha) | growth inhibition (%) | phyto-toxicity |
|---|---|---|---|
| 1 | 2.5 | 25 | no damages |
|  | 1.25 | 21 |  |
|  | 0.62 | 19 |  |
| 2 | 2.5 | 26 | " |
|  | 1.25 | 20 |  |
|  | 0.62 | 18 |  |
| 3 | 2.5 | 27 | " |
|  | 1.25 | 20 |  |
|  | 0.62 | 16 |  |
| 4 | 2.5 | 30 | " |
|  | 1.25 | 22 |  |
|  | 0.62 | 19 |  |
| 17 | 2.5 | 29 | " |
|  | 1.25 | 21 |  |
|  | 0.62 | 17 |  |
| 18 | 2.5 | 27 | " |
|  | 1.25 | 19 |  |
|  | 0.62 | 17 |  |
| 19 | 2.5 | 30 | " |
|  | 1.25 | 22 |  |
|  | 0.62 | 18 |  |
| 21 | 2.5 | 31 | " |
|  | 1.25 | 21 |  |
|  | 0.62 | 17 |  |
| 24 | 2.5 | 31 | " |
|  | 1.25 | 20 |  |
|  | 0.62 | 16 |  |
| 25 | 2.5 | 26 | " |
|  | 1.25 | 20 |  |
|  | 0.62 | 16 |  |
| 27 | 2.5 | 27 | " |
|  | 1.25 | 19 |  |
|  | 0.62 | 16 |  |
| 29 | 2.5 | 26 | " |
|  | 1.25 | 20 |  |
|  | 0.62 | 16 |  |
| 33 | 2.5 | 27 | " |
|  | 1.25 | 21 |  |
|  | 0.62 | 18 |  |
| 34 | 2.5 | 30 | " |
|  | 1.25 | 22 |  |
|  | 0.62 | 19 |  |
| 40 | 2.5 | 27 | " |
|  | 1.25 | 23 |  |
|  | 0.62 | 19 |  |
| 42 | 2.5 | 31 | " |
|  | 1.25 | 22 |  |
|  | 0.62 | 19 |  |
| 49 | 2.5 | 32 | " |
|  | 1.25 | 25 |  |
|  | 0.62 | 18 |  |
| 52 | 2.5 | 31 | " |
|  | 1.25 | 22 |  |
|  | 0.62 | 17 |  |
| 53 | 2.5 | 33 | " |
|  | 1.25 | 25 |  |
|  | 0.62 | 19 |  |
| 54 | 2.5 | 29 | " |
|  | 1.25 | 24 |  |
|  | 0.62 | 17 |  |
| 58 | 2.5 | 29 | " |
|  | 1.25 | 23 |  |
|  | 0.62 | 18 |  |
| 59 | 2.5 | 27 | " |
|  | 1.25 | 21 |  |
|  | 0.62 | 16 |  |
| 64 | 2.5 | 29 | " |

TABLE II-continued

| Compound of Ex. No. | dosage (kg/ha) | growth inhibition (%) | phyto-toxicity |
|---|---|---|---|
|  | 1.25 | 21 |  |
|  | 0.62 | 16 |  |
| 67 | 2.5 | 30 | " |
|  | 1.25 | 22 |  |
|  | 0.62 | 18 |  |
| 68 | 2.5 | 29 | " |
|  | 1.25 | 25 |  |
|  | 0.62 | 17 |  |
| 73 | 2.5 | 29 | " |
|  | 1.25 | 24 |  |
|  | 0.62 | 16 |  |
| 75 | 2.5 | 30 | " |
|  | 1.25 | 25 |  |
|  | 0.62 | 17 |  |
| 77 | 2.5 | 29 | " |
|  | 1.25 | 24 |  |
|  | 0.62 | 16 |  |
| 79 | 2.5 | 30 | " |
|  | 1.25 | 24 |  |
|  | 0.62 | 18 |  |
| 81 | 2.5 | 29 | " |
|  | 1.25 | 23 |  |
|  | 0.62 | 18 |  |
| 82 | 2.5 | 29 | " |
|  | 1.25 | 21 |  |
|  | 0.62 | 16 |  |
| 88 | 2.5 | 27 | " |
|  | 1.25 | 19 |  |
|  | 0.62 | 16 |  |
| 90 | 2.5 | 27 | " |
|  | 1.25 | 20 |  |
|  | 0.62 | 16 |  |
| 105 | 2.5 | 26 | " |
|  | 1.25 | 19 |  |
|  | 0.62 | 16 |  |
| 108 | 2.5 | 27 | " |
|  | 1.25 | 20 |  |
|  | 0.62 | 16 |  |
| 109 | 2.5 | 27 | " |
|  | 1.25 | 21 |  |
|  | 0.62 | 17 |  |
| 111 | 2.5 | 31 | " |
|  | 1.25 | 25 |  |
|  | 0.62 | 19 |  |
| 114 | 2.5 | 31 | " |
|  | 1.25 | 24 |  |
|  | 0.62 | 18 |  |

3. Growth inhibition of soya beans

Approximately 10 cm tall soya beans are sprayed with the preparations containing the active substance until dripping wet. Assessment takes place after 3 weeks.

Growth inhibition is expressed as a percentage, 100% denoting that growth has halted and 0% denoting a growth corresponding to that of the untreated control plants.

TABLE III

| Compound of Ex. No. | dosage (kg/ha) | growth inhibition (%) | phyto-toxicity |
|---|---|---|---|
| 1 | 2.5 | 25 | no damages |
| 2 | 2.5 | 24 | " |
| 3 | 2.5 | 26 | " |
| 4 | 2.5 | 27 | " |
| 17 | 2.5 | 24 | " |
| 18 | 2.5 | 23 | " |
| 19 | 2.5 | 28 | " |
| 21 | 2.5 | 27 | " |
| 24 | 2.5 | 22 | " |
| 25 | 2.5 | 22 | " |
| 27 | 2.5 | 24 | " |
| 29 | 2.5 | 19 | " |
| 33 | 2.5 | 26 | " |
| 34 | 2.5 | 24 | " |
| 40 | 2.5 | 21 | " |

TABLE III-continued

| Compound of Ex. No. | dosage (kg/ha) | growth inhibition (%) | phyto-toxicity |
|---|---|---|---|
| 42 | 2.5 | 26 | " |
| 49 | 2.5 | 29 | " |
| 52 | 2.5 | 27 | " |
| 53 | 2.5 | 22 | " |
| 54 | 2.5 | 25 | " |
| 58 | 2.5 | 26 | " |
| 59 | 2.5 | 23 | " |
| 64 | 2.5 | 24 | " |
| 67 | 2.5 | 22 | " |
| 68 | 2.5 | 25 | " |
| 73 | 2.5 | 27 | " |
| 75 | 2.5 | 31 | " |
| 77 | 2.5 | 25 | " |
| 79 | 2.5 | 21 | " |
| 81 | 2.5 | 24 | " |
| 82 | 2.5 | 27 | " |
| 88 | 2.5 | 27 | " |
| 90 | 2.5 | 22 | " |
| 105 | 2.5 | 21 | " |
| 108 | 2.5 | 23 | " |
| 109 | 2.5 | 27 | " |
| 111 | 2.5 | 23 | " |
| 114 | 2.5 | 25 | " |
| CCC | 2.5 | 10 | " |

4. Synergistic effects

A piece of open field, growing a variety of cereals, is selected for a small plot test with the compounds according to the invention. Subsequently, in the postemergence process, the growth regulators are applied to plants in various development stages using a water application rate of 400 liters/ha to 10 m² test plots. In each case the application is repeated 4 times. Assessment takes place two weeks after application, phytotoxicity, height of growth, development progress and yield components being assessed. It transpires that mixtures of the growth regulators of formula (I) in combination with an active substance of formula (IV), (V) or (XII) exhibit outstanding synergistic effects. A considerably more enhanced stem shortening is achieved than would have been expected from the activity of the components on their own (additive effect). This synergistic activity occurs in a wide range of plant development.

We claim:

1. A salt of a 1-phenylimidazole-5-carboxylic acid of formula (I)

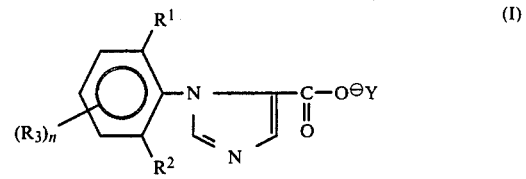

wherein
the symbols have the following meanings:
Y is

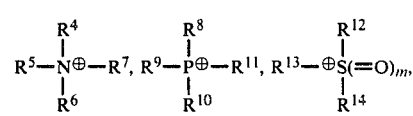

the argininium ion or the guanidinium ion
n is 0, 1, 2, or 3;
m is 0 or 1;
$R^1$, $R^2$ independently of each other are $C_1$–$C_4$-alkyl;

$R^3$ is $C_1$-$C_4$-alkyl, $C_1$-$C_4$-alkoxy or halogen, wherein the substituents can also be different, if n>1;

$R^4$, $R^5$, $R^6$ independently of each other, are H; $C_1$-$C_{18}$-alkyl, unsubstituted or mono-, di- or tri-substituted by halogen, $C_1$-$C_6$-alkoxy, [$C_1$-$C_6$-alkoxy]$C_2$-$C_4$-alkoxy, cyclo-$C_3$-$C_7$-alkyl, bicyclo-$C_7$-$C_{10}$ alkyl, benzyloxy, halobenzyloxy, methylbenzyloxy, benzyloxy-$C_2$-$C_4$-alkoxy, phenyl, halophenyl, methylphenyl, cyano, hydroxyl, formyl, $C_1$-$C_4$-alkylcarbonyl, carboxyl, $C_1$-$C_6$-alkoxycarbonyl, carbamoyl, phosphinyl, phosphonyl, $C_1$-$C_4$ alkylaminophosphonyl, di-$C_1$-$C_4$-alkylaminophosphonyl, amino, $C_1$-$C_6$-alkylamino, di-$C_1$-$C_6$-alkylamino, amino-$C_1$-$C_4$-alkylamino, $C_1$-$C_6$-alkylthio, phenylthio, phenoxy, furyl, tetrahydrofuryl, imidazolyl or triazolyl; $C_3$-$C_6$-alkenyl, unsubstituted or substituted by halogen or phenyl; $C_3$-$C_6$-alkynyl; cyclo-$C_3$-$C_8$-alkyl, unsubstituted or substituted by $C_1$-$C_4$-alkyl or halogen; cyclo-$C_5$-$C_6$-alkenyl; phenyl, unsubstituted, or mono-, di- or tri-substituted by halogen, nitro, cyano, $C_1$-$C_4$-alkyl, $C_1$-$C_4$-alkoxycarbonyl or $C_1$-$C_4$-alkoxy; or $R^4$ and $R^5$ together with the N form a 5- to 8-membered saturated heterocyclic amino group in which, in addition to the one N, up to 2 C can also be replaced by N, S or O, and which is unsubstituted or substituted by $C_1$-$C_4$-alkyl, halogen, phenyl, benzyl, oxo, amino, $C_1$-$C_4$-alkylamino, di-$C_1$-$C_4$-alkylamino, amino-$C_1$-$C_4$-alkyl, hydroxyl, hydroxy-$C_1$-$C_4$-alkyl, and $C_1$-$C_4$-alkoxy;

$R^7$ is H; a $C_1$-$C_{12}$-alkyl, unsubstituted or substituted by phenyl, halophenyl or methylphenyl; or if $R^4$, $R^5$ and $R^6$=H, amino, $C_1$-$C_4$ alkylamino, di-$C_1$-$C_4$-alkylamino, benzylamino, anilino, formylamino, $C_1$-$C_4$-alkylcarbonylamino, benzoylamino, hydroxyl, $C_1$-$C_6$-alkoxy or

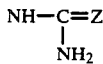

in which Z=O, S or NH; the exceptions being those compounds in which $R^4$, $R^5$, $R^6$ and $R^7$=H;

$R^8$, $R^9$, $R^{10}$, $R^{11}$ independently of each other are $C_1$-$C_{18}$-alkyl; phenyl, unsubstituted or substituted by halogen, $C_1$-$C_4$-alkoxy; or benzyl, unsubstituted or substituted by halogen, $C_1$-$C_4$-alkyl or $C_1$-$C_4$-alkoxy; and $R^{12}$, $R^{13}$, $R^{14}$ independently of each other are $C_1$-$C_6$-alkyl, phenyl, halophenyl, methylphenyl, benzyl, halobenzyl or methylbenzyl.

2. A composition for regulating plant growth comprising as an active component a plant growth regulating effective amount of at least one compound of formula (I) as claimed in claim 1 and an inert carrier.

3. A method for growth regulation of plants, which comprises applying to the plants or to the crop area an effective amount of at least one compound of formula (I) as claimed in claim 1.

4. A compound of formula (I) as claimed in claim 1 wherein

Y=

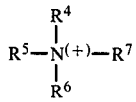

$R^4$, $R^5$, $R^6$ and $R^7$ having the meanings as defined in claim 1.

5. The compound 2-cloroethyltrimethylammonium 1-(2,6-diethylphenyl)imidazole-5-carboxylate.

6. The compound 3-Methoxypropylammonium 1-(2,6-diethylphenyl)imidazole-5-carboxylate.

7. The compound Tris(3-hydroxyethyl)ammonium 1-(2,6-diethylphenyl)imidazole-5-carboxylate.

8. The compound Piperidinium 1-(2,6-diethylphenyl)imidazole-5-carboxylate.

9. A compound of formula (I) as claimed in claim 1 wherein $R^8$, $R^9$, $R^{10}$, $R^{11}$ independently of each other are $C_1$-$C_{18}$-alkyl or phenyl, and $R^{12}$, $R^{13}$, $R^{14}$ are $C_1$-$C_6$-alkyl.

* * * * *

UNITED STATES PATENT AND TRADEMARK OFFICE
CERTIFICATE OF CORRECTION

PATENT NO.   :   4,775,406
DATED        :   October 4, 1988
INVENTOR(S)  :   Schmierer et al.

It is certified that error appears in the above-identified patent and that said Letters Patent is hereby corrected as shown below:

On the Title Page, in the section "[75] Inventors" change "Büstell" to --Bürstell--, Signed and Sealed this Twenty-sixth Day of December, 1989

Attest:

JEFFREY M. SAMUELS

*Attesting Officer*        *Acting Commissioner of Patents and Trademarks*